United States Patent [19]
Faeser et al.

[11] Patent Number: 4,799,866
[45] Date of Patent: Jan. 24, 1989

[54] SPRAY PUMP WITH A MOTOR DRIVEN DRIVE ROD

[75] Inventors: Ulrich Faeser, Kronberg; Dieter Mahn, Bad Homburg v.d.H., both of Fed. Rep. of Germany

[73] Assignee: Fresenius AG, Bad Homburg, Fed. Rep. of Germany

[21] Appl. No.: 865,732

[22] PCT Filed: Aug. 1, 1985

[86] PCT No.: PCT/DE85/00259
§ 371 Date: May 27, 1986
§ 102(e) Date: May 27, 1986

[87] PCT Pub. No.: WO86/01117
PCT Pub. Date: Feb. 27, 1986

[30] Foreign Application Priority Data
Aug. 3, 1984 [DE] Fed. Rep. of Germany ....... 3428655

[51] Int. Cl.$^4$ .................................... F04B 13/00
[52] U.S. Cl. .................................... 417/415; 604/155; 222/333; 222/390
[58] Field of Search ................... 604/154, 155; 128/DIG. 1; 417/415, 319; 222/390, 333; 74/424.8 A, 405; 192/94

[56] References Cited
U.S. PATENT DOCUMENTS

| | | | |
|---|---|---|---|
| 2,702,547 | 2/1955 | Glass | 128/218 |
| 4,191,187 | 3/1980 | Wright | 128/DIG. 1 |
| 4,255,096 | 3/1981 | Coker, Jr. et al. | 417/415 |
| 4,424,720 | 1/1984 | Bucchianeri | 604/155 X |

*Primary Examiner*—Carlton R. Croyle
*Assistant Examiner*—Eugene L. Szczecina, Jr.
*Attorney, Agent, or Firm*—Pravel, Gambrell, Hewitt, Kimball & Krieger

[57] ABSTRACT

A spray pump for metered delivery of a liquid from a spray cylinder by means of a spray piston having a motor-driven screwed-shaft gear unit located in a housing, the movably supported drive element of which can be brought into engagement with the movable spray part outside the housing. To ensure that the smooth-running characteristics of the spray pump are not impaired by dirt on a threaded shaft of the screwed-shaft gear unit, the threaded shaft is arranged and supported inside the housing. Moreover, for this purpose the drive element is passed through the wall of the housing and is supported movably around its longitudinal axis in the housing for actuation of the coupling.

8 Claims, 5 Drawing Sheets

SPRAY PUMP WITH A MOTOR DRIVEN DRIVE ROD

The present invention relates to a motor-driven spray pump.

Spray pumps are used in the clinical field and in medical research to administer fairly small amounts of liquid to the patient over a fairly long period of time.

U.S. Pat. No. 4,191,187 discloses a motor-driven spray pump.

This publication acquaints us with a spray pump for metered delivery of a liquid from a spray cylinder by means of a spray piston with at least one interchangeable spray.

This familiar spray pump has a housing with a mounting support for the spray and a motor drive with a screwed-shaft gear unit for transmission of the driving power of the motor from the drive unit to the spray. At the same time, the screwed-shaft gear unit has an axially movable drive element, one end of which can be made to engage the movable spray piston outside the housing, in order to move the spray part translationally. Furthermore, a translationally movable coupling is arranged in a bearing block and has a stop link with a threaded section, to make it possible to establish drive linkage between the drive element and the spray part. Moreover, the bearing block supports an elongated guide piece arranged in the sliding seat on the threaded shaft, the stop link of the coupling being movably supported on the guide piece and/or on the bearing block, and the stop link also being a coupling pin movably supported diagonally to the threaded shaft, with an essentially U-shaped recess running at right angles to its longitudinal axis, through,, which at least part of the circumference of the threaded shaft extends. And the threaded section is located on one side of the U-shaped recess.

The main disadvantage of a spray pump of this type, however, is that the whole length of the threaded shaft is arranged outside the housing. This causes a problem in that the threaded shaft becomes contaminated very easily in operation, thereby involving the risk that the smooth running of the guide piece or the drive element connected to it, so necessary for precise metering, will be impaired, there even being a danger that if heavy contamination builds up, movement will be totally impossible. This in turn leads to the problem of a spray pump of this type, especially in continuous operation having to be checked frequently with regard to functional efficiency, which greatly limits its usefulness in practical operation.

The problem facing the invention, therefore, is to produce a motor-driven spray pump in which smooth running of the gearing and a margin of functional safety are always guaranteed, even in continuous operation.

This problem is solved as described briefly below, and as described in more detail in the Detailed Description of the Preferred Embodiment.

What is first achieved, is that the whole length of the threaded shaft can be accommodated and supported in the housing, so that there is no risk of the threaded shaft being contaminated in any way, which might otherwise lead to the problems previously explained, given the state of the art in this area.

By arranging the drive element and its pivoting in the housing, it also becomes possible to operate a coupling from outside while retaining its simple design, so that making or breaking the drive connection is possible just as easily as with the state of the art in this area.

The drive element of the spray pump according to the invention is indeed drawn outside the housing partially at times when the spray piston is retracted, yet no contamination problems comparable to the state of the art in this area occur at this time, since, for one thing, the surface of the drive element can be designed very smooth, and, for another, only part of it has to be accommodated outside the housing. If the spray pump according to the invention is not being operated, the drive element, over and above that, can be accommodated wholly in the housing, which is not possible given the state of the art in this area as far as its threaded shaft is concerned, since the whole length of the latter is permanently located outside the housing.

From WO No. 82/01998 (the U.S counterpart of which is U.S. Pat. No. 4,424,720) we are indeed familiar with a spray pump of which the threaded shaft is arranged inside the housing. This threaded shaft, however, is supported at one end outside the housing, for which purpose a guide rod connected to the threaded shaft in one piece is provided, the whole length of it being permanently outside the housing. Again, the drive element of this spray pump is supported and can slide on this guide rod, so that the advantage of arranging the threaded shaft inside the housing is cancelled out again, to a considerable extent at least. The reason for this is that this familiar spray pump requires two additional seals: one between the guide rod and the drive element and the second between the drive element and the housing. Smooth operation is thereby considerably reduced, since in order to maintain the satisfactory operation of a spray pump of this kind, double seals with a scraper ring and a seal ring are used, considerably impeding operation of the spray pump. Over and above that, specifications concerning accuracy of fit for this spray pump are very stringent, since it has multiple guideways at the places previously mentioned, between guide rod, drive element and housing, where the absence of accurate fit, cant may easily occur. This is precisely what is avoided in the spray pump according to the invention, as it requires just one guide for the drive element, so that even if specifications regarding accuracy of fit are less stringent, cant cannot occur. Furthermore, the coupling of the spray pump familiar from WO No. 82/01998 is completely different in design from that of the spray pump according to the invention, so that comparable conditions do not, exist.

Based on the U.S. Pat. No. 2,702,547 type model, according to FIG. 1 therein, we are indeed also familiar with the arrangement of the threaded shaft inside the housing, this spray pump having a coupling very similar to the state of the art in this area. However, for operation of the coupling and to guarantee mobility of the drive element, an elongated recess is provided in the housing, so that in the end the threaded rod may become heavily contaminated even with this familiar spray pump, which leads to the same problems as with the generic spray pump.

For geared conversion of the rotation of the drive element to a translational movement of the stop link, according to a further refinement of the invention a control element is provided, located between the drive element and the stop link. This control element has the form of a pivoting disk, appropriately located on the drive element and attached to it, and having a dog engaging the stop link. Simple in design, a pin arranged eccentrically to the axis of rotation of the disk is provided as the dog, engaging a corresponding recess of the stop link. Depending on how far the pin is positioned from the axis of rotation, appropriate gearing can be achieved in the conversion of rotation into translational movement. Further details, features and advantages of the invention are evident from the following description of type models of the invention and specific embodiments thereof with the aid of the drawings.

DESCRIPTION OF THE PREFERRED EMBODIMENT

Figure 1:
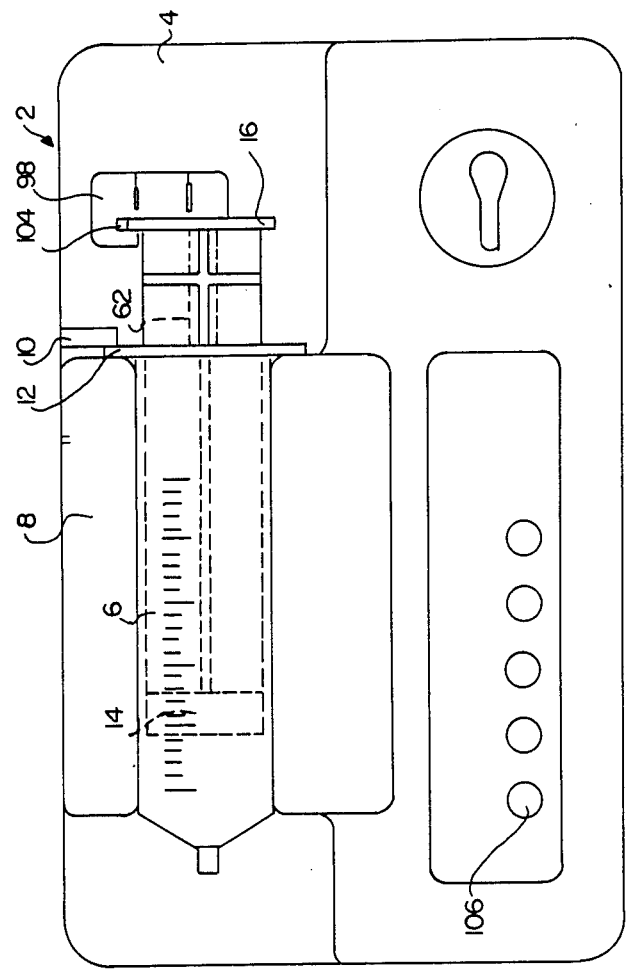
FIG. 1 shows a top view of a spray pump.
Figure 2:
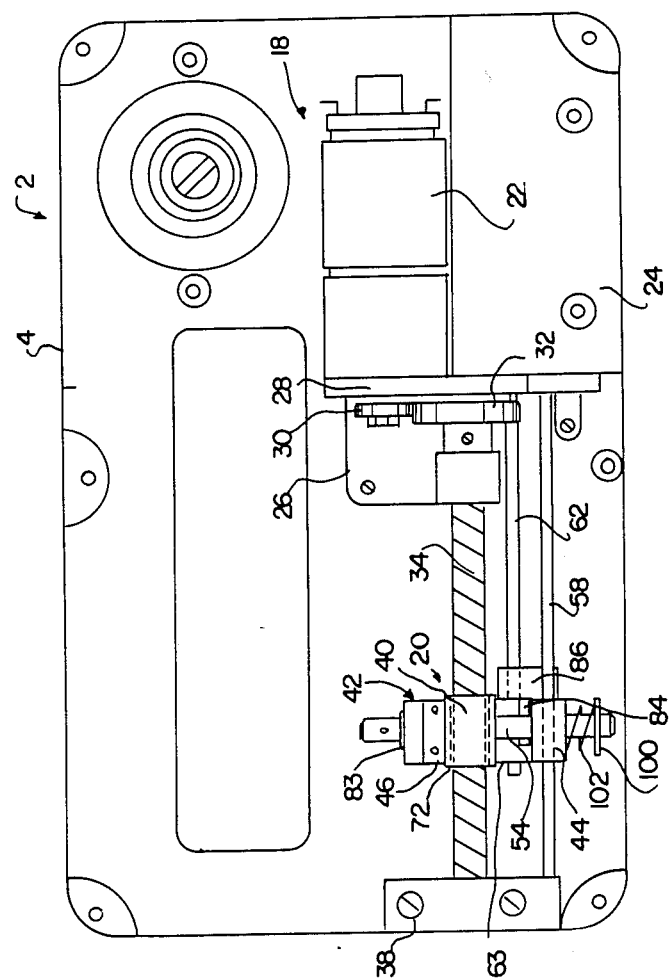
FIG. 2 is an inverted plan view of the spray pump according to FIG. 1.

Spray pump 2, represented in FIGS. 1 and 2, has a housing 4 the top of which is equipped with a mounting 8 partially surrounding the circumference of a spray body 6. The spray is secured endwise in mounting 8 by means of a spray body 6 shoulder 12 attached between a bracket 10 and mounting 8.

Figure 3:
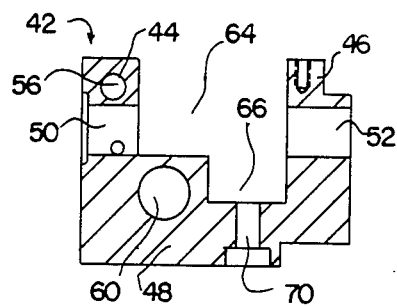
FIG. 3 is a side view of a bearing block.

Inside housing 4, as can be seen in FIG. 2, a drive 18 and a gear unit 20 connected to it are accommodated. An electric motor 22 is provided as the drive here, screwed on to a bearing block 26 mounted on a bracket 24. Motor shaft 28 bears a pinion 30 meshing with a gear wheel 32, which is arranged so as to rotate fixed to a threaded shaft 34. Threaded shaft 34 represents part of gear unit 20, which conveys the drive motion of drive 18 to spray piston 14. Threaded shaft 34 is aligned parallel to motor shaft 28, one end of it pivoting in bearing block 26, while the other end is held by a bearing block 38 attached to the opposite wall of the housing, able to rotate and axially immovable. Another component of gear unit 20 is an elongated guide piece 40 located on threaded shaft 34. A bearing block 42 is provided as a mounting for guide piece 40, being represented as a component in FIG. 3.

Bearing block 42 is essentially U-shaped in design and has two sides, 44 and 46, and a base 48. Drill holes 50 and 52 are provided in the two sides 44 and 46 of guide piece 42 and directed toward each other, a stop link 54 (FIG. 4) designed as a coupling pin being accommodated in them. At right angles to drill holes 50 and 52, a further drill hole 56 is provided in side 44, and receives a torsional locking rod 58 (FIG. 2), arranged parallel to threaded shaft 34, and fixed in housing 4 in bearing blocks 26 and 28. A drill hole 60 provided parallel to drill hole 56 in base 48 of bearing block 42 receives the end of drive element 62 (FIG. 1), designed as a driving rod, and oriented parallel to torsional locking rod 58 (FIG. 2), allowing the drive element 62 to pivot about its longitudinal axis. Drive element 62 is held in an, axial direction by means of a retaining ring 63 (FIG. 2) seated in an annular tee slot of drive element 62. A cavity 66 is provided in a U-shaped recess 64 of bearing block 42, guide piece 40 being accommodated and secured in it. To secure guide piece 40 there is at the same time a drill hole 70 piercing base 48, through which a bolt (not represented here) can be passed, to engage a thread provided on the bottom of guide piece 40. Guide piece 40 has a drill hole 72 running parallel to drill holes 56 and 60 (indicated with a broken line in FIG. 2) through which threaded shaft 34 passes with a sliding seat. Thus threaded shaft 34 and guide piece 40 form a stable guideway for bearing block 42 and stop link 54. Distortion of the arrangement is prevented by torsional locking rod 58, which passes through drill hole 56 with some free movement.

Figure 4:
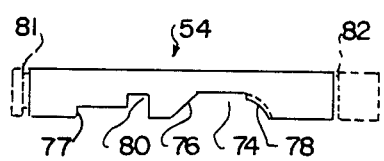
FIG. 4 shows a stop link designed as a coupling pin which, as can be seen in FIG. 1, is accommodated in the drill holes in the sides of the bearing block.
Figure 7:
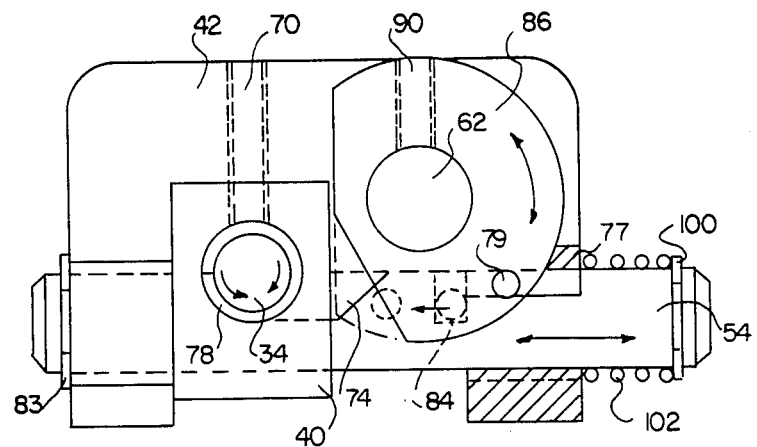
FIG. 7 is an enlarged, partially cut-away representation of the bearing block with the stop link and the control element.
Figure 8:
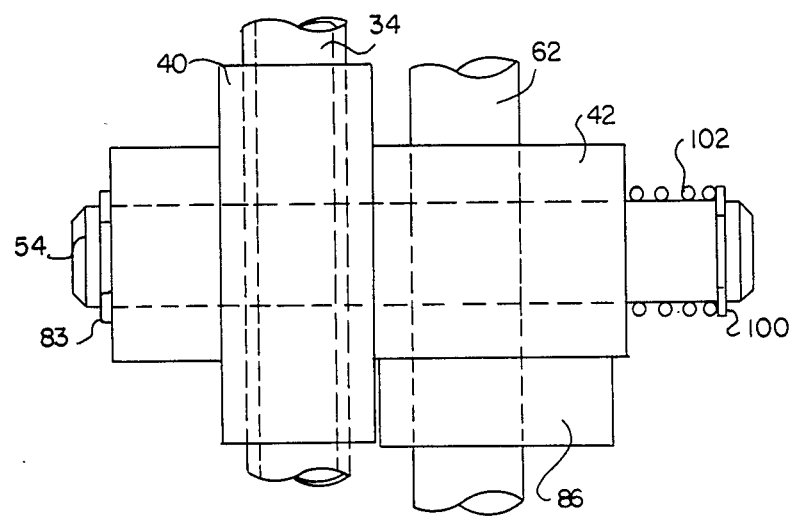
FIG. 8 is an inverted plan view of the bearing block represented in FIG. 7 with stop link and control element.

Stop link 54, represented as a component in FIG. 4 and designed as a coupling pin, has a recess 74 running at right angles to its longitudinal axis and bounded axially on one side by a wall 76 running oblique to the axis and on the other side by a threaded section 78. Part of the circumference of threaded shaft 34 is arranged in this recess 74, so that the thread of threaded shaft 34 can be made to engage threaded section 78. The axial length of recess 74 is selected so that when stop link 54 moves axially, the thread of threaded shaft 34 completely disengages threaded section 78, before stop link 54 abuts a shoulder 77 on a pin 79 (FIG. 7). As well as recess 74, another recess 80 is provided in stop link 54. This recess 80 is engaged by a pin 84 extending axially which is solidly connected to a control element 86 located on and rotating with drive element 62. Stop link 54 has annular tee slots 81 and 82 on its ends, in one of which a retaining ring 83 (FIG. 2) fits, limiting the length of movement of stop link 54.

Figure 5:
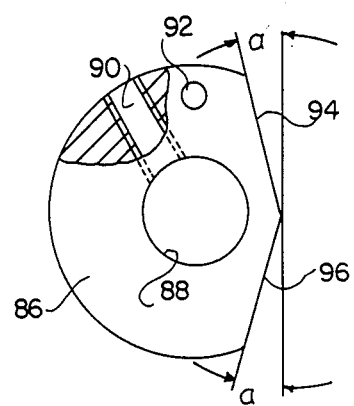
FIG. 5 is a side view of a control element.
Figure 6:
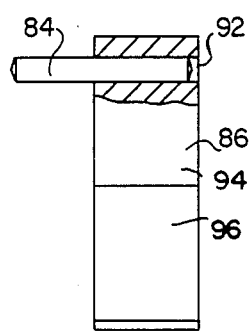
FIG. 6 is a front view of the control element according to FIG. 5.

Control element 86 is represented as a component in FIGS. 5 and 6. It consists of a circular segment which has a central drill hole 88 through which drive element 62 passes. In order to connect control element 86 so as to be tight in rotation with drive element 62, a radial tapped hole 90 is provided in control element 86, into which a screw (not represented) can be threaded, and by means of which control element 86 is clamped to drive element 62. Another drill hole 92 is provided eccentric to drill hole 88, the former receiving pin 84. Pin 84 is tightly fitted in drill hole 92, with force fit, for example, and extends parallel to the axis of drill hole 88. In order to facilitate a compact arrangement, disk-shaped control element 86 is segmented in design, forming intersection planes 94 and 96 adjacent to drill hole 88. Planes 94 and 96 run, relative to a plane running parallel to the plane containing the axes of drill holes 88 and 92, under an acute angle $\alpha$ of 15° especially.

The method of operation of spray pump 2 is described in greater detail below. In order to make spray pump 2 ready for operation, a spray body 6 filled with a liquid is secured in mounting 8. In this position spray piston 14 is drawn relatively far out of sprayer body 6. In order to make connecting piece 98, which is solidly joined to drive element 62, engage pressure plate 16 (FIG. 1) of spray piston 14, drive element 62 must be retracted a corresponding distance. For this purpose it is necessary first to disconnect drive element 62 from drive 18 by means of stop link 54. To do this, drive element 62 is rotated around its longitudinal, axis by manually rotating of connecting piece 98. Control element 86, which is solidly joined to drive element 62, is likewise rotated around the longitudinal axis at the same time, so that pin 84 connected to it swivels through an arc around that axis. At the same time, the rotation is converted into a translational movement of stop link 54, pin 84 engaging recess 80 of it (see FIG. 7). At the same time, stop link 54 is moved against a supported spring 102 arranged concentrically around the end of stop link 54 projecting from bearing block 42, connected on one side to bearing block 42 and on the other side to a spring plate 100 connected to stop link 54 and set in annular tee slot 81, so that threaded section 78 of stop link 54 disengages the thread of threaded shaft 34. Drive element 62 can then be retracted an appropriate distance, so that a radial slot 104 (FIG. 1) provided in connecting piece 98 can be made to engage pressure plate 16. For this purpose, connecting piece 98 only needs to be released with appropriate axial alignment. Because of the strength of spring 102, stop, link 54 is thereby made to engage the threaded shaft 34 again, and control element 86, and drive element 62 along with it, return to their original position, slot 104 on connecting piece 98 holding the edge of pressure plate 16.

The operation of spray pump 2 then takes place by switching on electric motor 22 by means of a switch 106 provided at the top of the housing 4. As a result of the rotation of motor shaft 28 of electric motor 22, threaded shaft 34 is driven through pinion 30 and gear wheel 32, so that bearing block 42 and guide piece 40 move along threaded shaft 34. Since drive element 62 is fixed axially in bearing block 42, it is taken along, and so moves spray piston 14 into the sprayer body 6. After electric motor 22 is switched off, the spray, as previously described, can easily be reset in the original position.

We claim:

1. An improved spray pump for metered delivery of a liquid from a spray cylinder by means of a spray piston, the spray pump having a housing, means for mounting the spray cylinder in the housing, a motor drive in driving connection with a threaded shaft mounted within the housing, and a gear unit for transmitting drive force from the threaded shaft to the spray piston, the gear unit having an axially movable drive rod extending through the wall of the housing, one end of the drive rod being engageable with the spray piston outside of the housing, the improvement comprising:

- a translationally movable coupling arranged in a bearing block to connect the drive rod to the threaded shaft, the coupling having a coupling pin provided with a threaded section, the coupling pin being displaceably mounted on the bearing block and having a U-shaped recess extending transversely to the longitudinal axis of the coupling pin with the threaded section disposed on the side wall of the recess to engage the threaded shaft;
- the drive rod being pivotably mounted around its longitudinal axis in the housing for actuating the coupling, the drive rod being at a distance from and parallel to the threaded shaft;
- a control element fixed to the drive rod and located between the drive rod and the coupling pin, the control element having a cam which engages the coupling pin and which is disposed eccentric to the axis of rotation of the control element; and
- a torsional locking rod being arranged parallel to and at a distance from the threaded shaft and the drive rod, the bearing block engaging and being movable along the torsional locking rod in a direction parallel to the longitudinal axis of the torsional looking rod.

2. The spray pump according to claim 1, wherein the end of the drive rod located outside the housing is equipped with a connecting piece.

3. The spray pump according to claim I, wherein the bearing block is of essentially U-shape design, one of the sides of the bearing block forming the U-shape having a drill hole to receive the torsional locking rod.

4. The spray pump according to claim 3, wherein both sides of the bearing block have drill holes in which the coupling pin is supported and axially movable.

5. The spray pump according to claim 3, wherein the bearing block has a drill hole in which the drive element, which can engage the movable spray piston, pivots and is axially immovable.

6. The spray pump according to claim 3, wherein a guide piece is secured in a U-shaped recess formed by the sides of the bearing block.

7. The spray pump of claim 1, wherein the control element is a pivotably mounted disc.

8. The spray pump of claim 1, wherein the cam is a receiving pin engaging a recess of the coupling pin.

* * * * *